United States Patent [19]

DeWoskin

[11] 4,157,719
[45] Jun. 12, 1979

[54] METHOD AND APPARATUS FOR ULTRASONIC SEALING AND CUTTING, AND TABS PRODUCED THEREBY

[75] Inventor: Irvin S. DeWoskin, St. Louis, Mo.

[73] Assignee: Beltx Corporation, Barnhart, Mo.

[21] Appl. No.: 769,546

[22] Filed: Feb. 17, 1977

[51] Int. Cl.² ............... B32B 31/18; B32B 31/20
[52] U.S. Cl. .................... 128/291; 24/202; 112/264.1; 156/73.3; 156/250; 156/290; 156/269; 156/510; 156/580.2; 428/103; 428/194; 428/282; 428/287
[58] Field of Search ........... 428/196, 200, 282, 286, 428/287, 298, 103, 193, 194; 24/202, 150 R; 128/291; 156/73.1, 73.2, 530, 580.1, 580.2, 268, 73.3, 250, 251, 510, 515, 290; 112/264

[56] References Cited

U.S. PATENT DOCUMENTS

| | | |
|---|---|---|
| 3,157,928 | 11/1964 | DeWoskin ...................... 24/150 R |
| 3,242,029 | 3/1966 | Deans .............................. 156/580.2 |
| 3,448,464 | 6/1969 | Jonas ................................ 24/150 R |
| 3,457,132 | 7/1969 | Tuma et al. ..................... 156/73.3 X |
| 3,558,381 | 1/1971 | Colianni .......................... 156/73.2 |
| 3,565,732 | 2/1971 | Colianni .......................... 112/264 |
| 3,666,599 | 5/1972 | Obeda .............................. 156/73.2 |
| 3,697,357 | 10/1972 | Obeda ............................ 156/510 |
| 3,817,802 | 6/1974 | Meyer ............................. 156/73.1 |

Primary Examiner—Michael G. Wityshyn
Attorney, Agent, or Firm—Koenig, Senniger, Powers and Leavitt

[57] ABSTRACT

A method of and apparatus for ultrasonically sealing and cutting workpieces wherein the workpiece is clamped between an anvil and an ultrasonic horn for being sealed and cut adjacent the seal by pressing a cutting edge into the workpiece from the anvil side of the workpiece while it is ultrasonically activated, particularly for making tabs for sanitary belts, and tabs made thereby of ultrasonically sealable fabric.

17 Claims, 16 Drawing Figures

METHOD AND APPARATUS FOR ULTRASONIC SEALING AND CUTTING, AND TABS PRODUCED THEREBY

BACKGROUND OF THE INVENTION

This invention relates to a method of and apparatus for ultrasonically sealing and cutting ultrasonically sealable workpieces, and more particularly to a method of and apparatus for manufacturing tabs for sanitary belts, and to improved tabs for such belts which may be made by the said method and apparatus.

The invention involves improved tabs for sanitary belts of the general type disclosed in U.S. Pat. No. 3,157,928 issued Nov. 24, 1964 and U.S. Pat. No. 2,904,046 issued Sept. 15, 1959, the improved tabs being made of fabric. The method and apparatus of the invention have been developed principally for manufacturing the improved tabs, but it is to be understood that the basic principles of the method and apparatus are applicable to the ultrasonic sealing and cutting of workpieces in general, and may be applied to the manufacture of other items. Thus, for example, it is contemplated that the basic principles of the method and apparatus of the invention may be utilized for ultrasonically forming buttonholes in polyester garments (polyester materials being ultrasonically sealable), as a replacement for sewing buttonholes.

SUMMARY OF THE INVENTION

Among the several objects of the invention may be noted the provision of an improved method of and apparatus for ultrasonically sealing and cutting ultrasonically sealable workpieces, and particularly for ultrasonically sealing and cutting tabs for sanitary belts; the provision of such a method and apparatus which enables sealing and cutting of a workpiece (e.g., a strip for forming tabs for sanitary belts) in a single operation, as distinguished from separate sealing and cutting operations, thereby increasing production rates; the provision of an improved tab having outer fabric layers for a sanitary belt; the provision of such a tab which keeps its shape and appearance after repeated use and washings; the provision of a tab which is soft and comfortable to wear yet durable; and the provision of such a tab which may be quickly and economically fabricated with little or no waste of material and which is adapted to be secured to a sanitary belt without stitching.

In general, the method of this invention involves clamping a workpiece (which is ultrasonically sealable) between an anvil and an ultrasonic horn, the anvil having a raised pattern corresponding to the seal to be made, ultrasonically powering the horn for ultrasonically sealing the workpiece where it is clamped against said raised pattern by the horn, and, while the workpiece is clamped and the horn is ultrasonically powered, pressing a cutting edge into the workpiece from the anvil side of the workpiece to cut through the workpiece while it is ultrasonically activated adjacent the ultrasonic seal made by the raised pattern.

Apparatus of this invention (adapted to carry out the stated method) generally comprises an anvil having a raised pattern corresponding to the seal to be made and an ultrasonic horn relatively movable toward and away from one another, the horn being adapted to clamp a workpiece against the raised pattern on the anvil when the horn and anvil are moved relatively toward one another. Means is provided for ultrasonically powering the horn for ultrasonically sealing the workpiece where it is clamped against the raised pattern by the horn. A cutter associated with the anvil is movable relative to the anvil to press its cutting edge into the workpiece from the anvil side of the workpiece to cut through the workpiece while it is ultrasonically activated adjacent the ultrasonic seal made by the raised pattern.

A tab of this invention comprises three layers of which the outer layers are of flexible ultrasonically sealable fabric and the intermediate layer is of flexible ultrasonically sealable padding material to constitute padding for the tab, the three layers being sealed together along each of their side edges and at each end thereof by a series of discrete thermoplastic stitches (i.e., fused stitches).

Tabs of the invention are made by combining three strips of flexible ultrasonically sealable material with the outer strips being of ultrasonically sealable fabric and the intermediate strip being of ultrasonically sealable padding material to constitute padding for the tabs, ultrasonically stitching the three strips together along their side edges, intermittently feeding the resultant composite strip forward a distance corresponding to the desired tab length with a dwell between successive feed cycles, clamping the composite strip between an anvil and an ultrasonic horn during each dwell, the anvil being formed ultrasonically to stitch the three strips of the composite strip together on two lines spaced lengthwise of the composite strip forming a trailing end seal of one tab and a leading end seal of the next tab, powering the horn to form said seals, and pressing a cutting edge into the composite strip between said lines from the anvil side of the composite strip while the horn is powered to cut through the composite strip between said seals.

Other objects and features will be in part apparent and in part pointed out hereinafter.

BRIEF DESCRIPTION OF THE DRAWINGS

Corresponding reference characters indicate corresponding parts throughout the several views of the drawings.

DESCRIPTION OF THE PREFERRED EMBODIMENT

Figure 1:
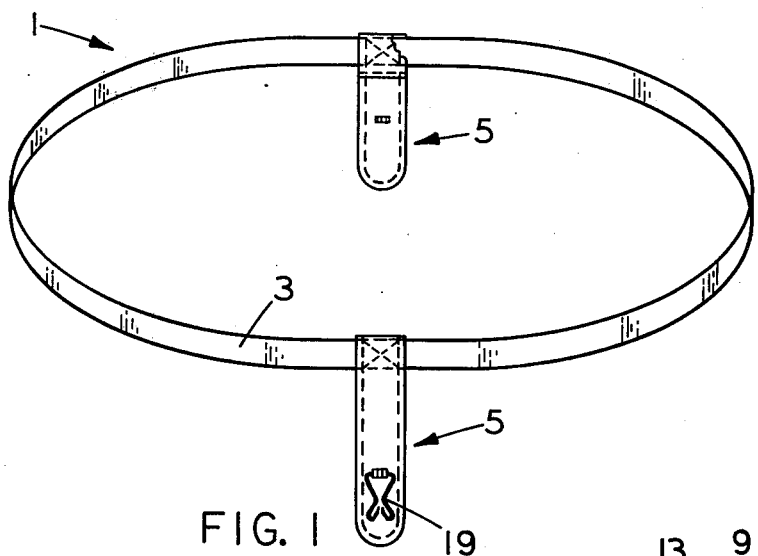
FIG. 1 is a perspective view showing a sanitary belt having front and back tabs made in accordance with this invention suspended therefrom.

Referring to the drawings, there is indicated at 1 in FIG. 1 a sanitary belt comprising an elastic waistband 3 from which depend front and back sanitary napkin supports or elongate tabs of this invention, each tab being designated 5. Each tab 5 comprises three layers of which the outer layers 7 and 9 are of flexible ultrasonically sealable fabric and the intermediate layer 11 is of flexible ultrasonically sealable padding material to constitute padding for the tab. The outer layers may be of any suitable ultrasonically sealable fabric, such as a polyester fabric, and all three layers are preferably of a nonwoven polyester fabric, such as a spun-bonded, polyethylene terephthalate fabric, and may be, for example, of the random nonwoven polyester fabric sold under the trade name NEXUS by Burlington Mills, with the intermediate layer 11 being of heavier loft than the outer layers to act as padding. The outer layers may be of woven satin polyester fabric (front and back), or the front layer may be a woven taffeta polyester fabric, and the intermediate layer 11 may be an ultrasonically sealable foamed plastic padding material, such as polyurethane. All three layers are ultrasonically stitched together one on another in continuous fashion along their side edges as indicated at 13 and at their top and bottom edges as indicated at 15 and 17 in accordance with this invention as will be hereinafter described.

A clasp 19 for gripping one end of a sanitary napkin is provided on each tab 5 as shown in the drawings. This is preferably of the type disclosed in U.S. Pat. No. Des. 198,682, issued July 21, 1964.

An end portion 21 of the tab is folded around the upper edge of the waistband 3 on a transverse top score line indicated at 23 so that the waistband is sandwiched between end portion 21 and an intermediate portion 25 of the tab with portion 21 on the inside and portion 25 on the outside of the band. The tab is ultrasonically sealed to the band (which may be comprised of any suitable commercially available ultrasonically sealable elastic material such as an elastic polyester material) by discrete thermoplastic stitches as indicated at 27, although it will be understood that tab 5 may also be sewn or otherwise secured to the band.

In accordance with this invention, the outer layers 7 and 9 of tabs 5 preferably have relatively hard outer surfaces for providing greater abrasion resistance and long tab life. Thus, they may have harder outer surfaces than the central layer 11 for this purpose.

The tab 5, comprising the three discrete layers of spun-bonded nonwoven fabric, is soft, comfortable to wear and may be readily laundered without losing its overall shape and appearance. As noted above, the fabric, being nonwoven, is not prone to ravelling and the edges of tab 5 need not be conventionally finished (e.g., as by serging), thus greatly simplifying the manufacturing process and reducing the cost.

Figure 2:
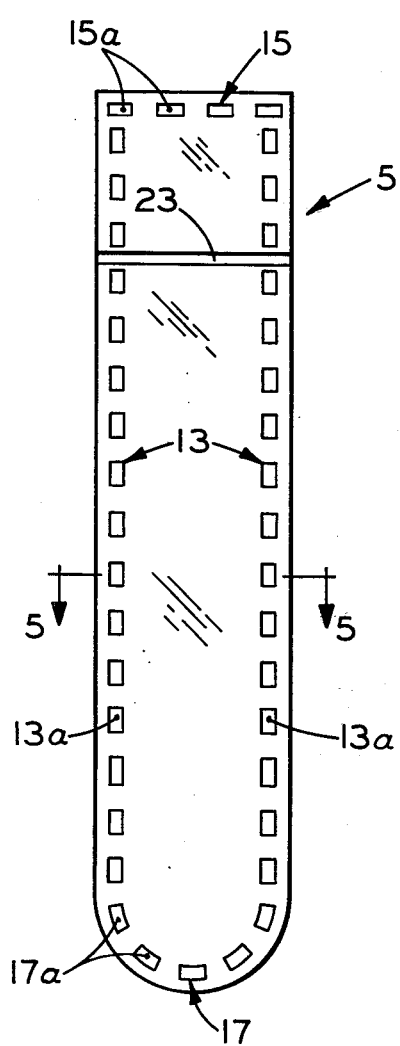
FIG. 2 is a view of a tab as produced, and before application of a gripper to the tab.
Figure 3:
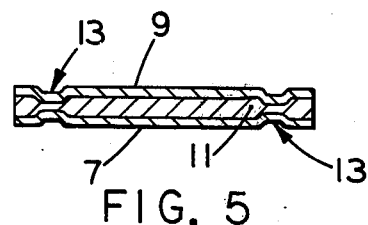
FIG. 3 is an enlarged fragment of FIG. 1 illustrating the front tab.
Figure 4:
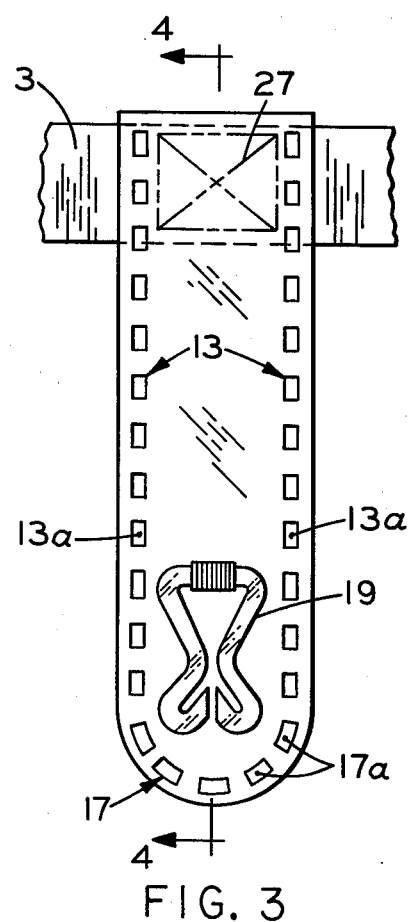
FIG. 4 is an enlarged horizontal section taken on line 4—4 of FIG. 3.
Figure 5:
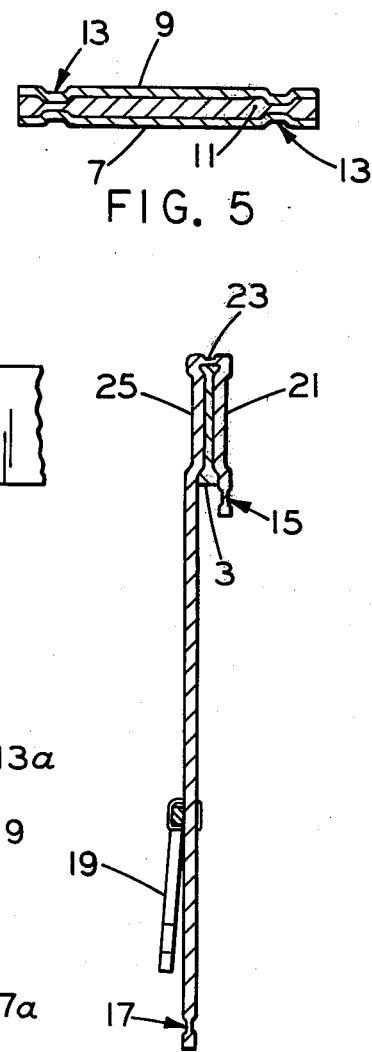
FIG. 5 is an enlarged vertical section taken on line 5—5 of FIG. 2.
Figure 6:
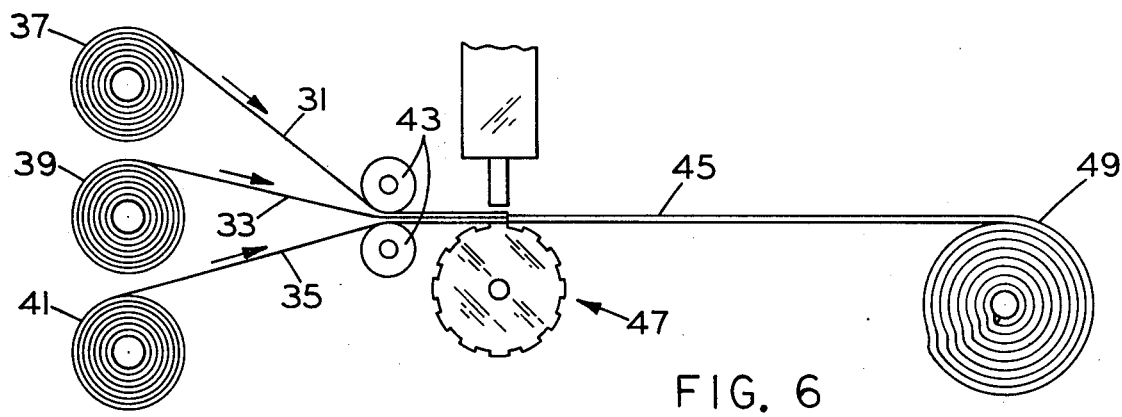
FIG. 6 is a diagrammatic side elevation illustrating certain initial procedure in the manufacture of tabs for sanitary belts in accordance with this invention.
Figure 7:
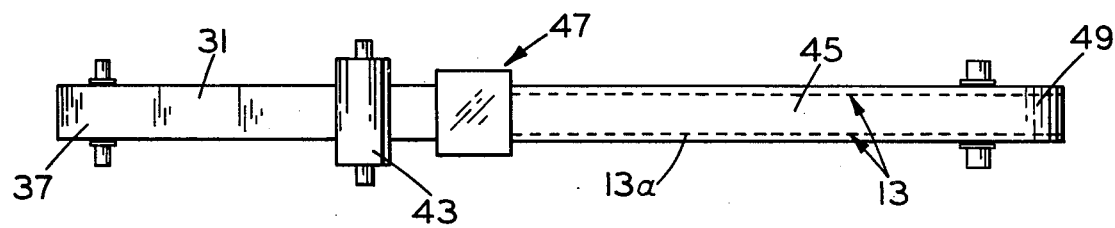
FIG. 7 is a plan view of FIG. 6.

FIGS. 6–12 illustrate the manufacture of tabs 5 in accordance with this invention. As shown in FIGS. 6 and 7, three continuous strips 31, 33, 35, of flexible nonwoven polyester material, for example, are drawn from respective supply rolls 37, 39, 41 by a pair of power driven feed rollers each designated 43, and combined one on top of the other for forming a composite strip 45 having a width identical to that of the finished tab 5. In this respect, strip 33 (corresponding to central layer 11 of tab 5) is preferably of heavier loft than strips 31, 35 (corresponding to outer layers 7, 9) of the tab. The composite strip 45 is continuously fed forward (to the right as viewed in FIGS. 6 and 7) and strips 31, 33, 35 are ultrasonically stitched together along their side edges by seals indicated at 13 extending along these edges. Each seal 13 is constituted by a continuous series of discrete thermoplastic stitches 13a as shown in FIG. 7, being made in accordance with the method of this invention by ultrasonically stitching the edges together. This ultrasonic stitching may be quickly, easily and efficiently carried out utilizing an ultrasonic sewing machine 47 such as the Model 300 Sonic Sewing Machine sold by Branson Sonic Power Company of Danbury, Connecticut, and such as disclosed in U.S. Pat. No. 3,666,599, issued May 30, 1972. The stitch used herein is formed by using a wheel such as indicated at 24 in FIG. 2 of said patent having the appropriate sewing pattern on its rim.

Figure 9:
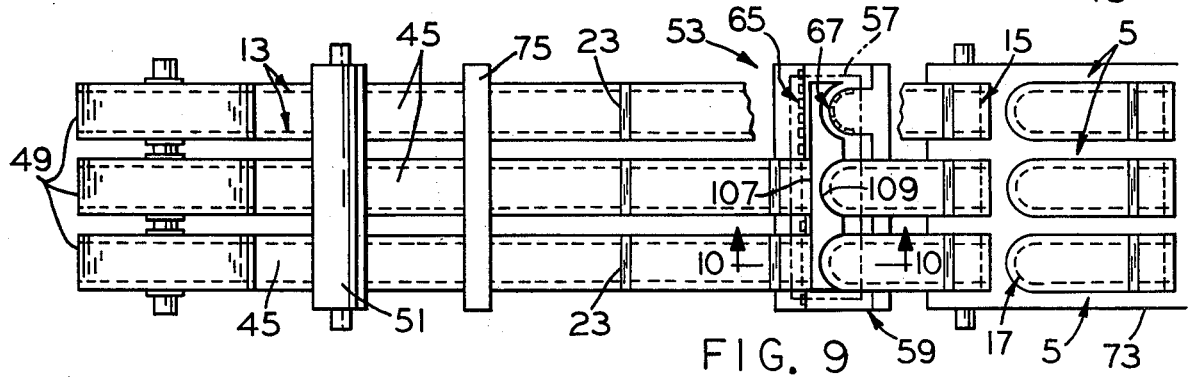
FIG. 9 is a plan of FIG. 8.
Figure 10:
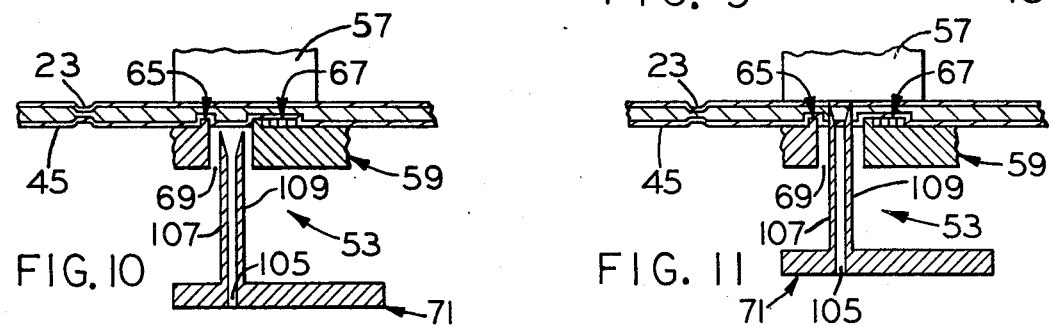
FIG. 10 is an enlarged horizontal section taken on line 10—10 of FIG. 9 showing a strip being ultrasonically end-sealed.
Figure 11:
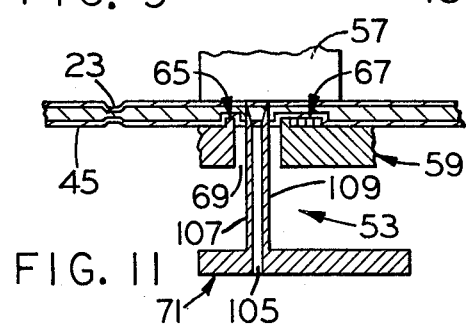
FIG. 11 is a view similar to FIG. 10 showing the strip being cut.
Figure 12:
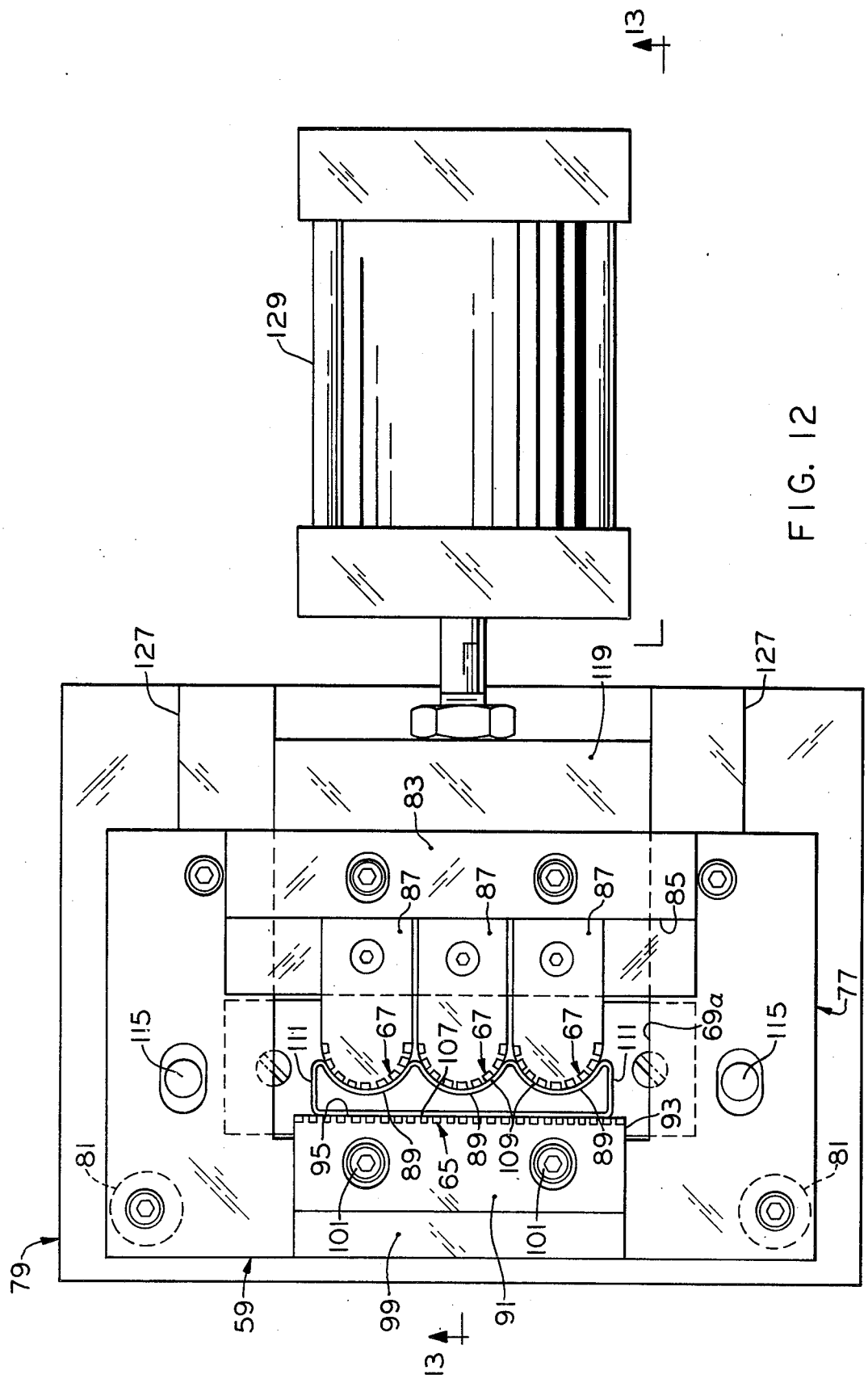
FIG. 12 is a plan of apparatus of this invention for the ultrasonic end sealing and cutting of the tabs.

After strips 31, 33, 35 have been sealed together along their side edges, the resultant three-layer composite strip 45 is wound up in a roll 49. A suitable number of rolls 49 (e.g., three as shown in FIG. 9) are then journalled in side-by-side relation and the strips 45 are unrolled from the rolls and intermittently fed forward by draw rolls indicated at 51 through an ultrasonic sealing and cutting apparatus of this invention generally indicated at 53 (FIGS. 9–14) a predetermined distance corresponding to the desired tab length, with a dwell between successive feed cycles. The ultrasonic apparatus 53 includes means for segmenting the strips 45 into individual tabs of the invention and comprises an ultrasonic electroacoustic transducer 55 which converts electrical power to mechanical vibratory power. The transducer 55 ultrasonically powers an ultrasonic horn 57 which is operable in conjunction with an anvil generally designated 59 having three sets of raised projections or teeth for forming ultrasonic end seals 15 and 17 for the tabs, end seal 15 being a straight-line seal extending transversely of the composite strip from one side thereof to the other, and end seal 17 being an arcuate (generally semicircular) seal extending from one side of the composite strip to the other. Each set of teeth comprises a raised pattern of teeth (i.e., a set of teeth projecting up from the upper face of the anvil) with the pattern comprising a straight line of teeth 65 for forming the straight-line seal 15 and an arcuate line 67 of teeth for forming the arcuate end seal 17. Line 65 is spaced from but adjacent the arcuate line of teeth on the convex side of the arcuate line of teeth, and there is an opening 69 in the anvil between the arcuate line 67 and the straight line 65 of teeth. Each tooth at 65 and each tooth at 67 is of narrow rectangular shape in plan so that the resultant individual seal or stitch which it forms, as indicated at 15a and 17a, is an elongate fused (and indented) area of the tab, typically about 1/16 inch long and 1/32 inch wide, with the teeth and hence the fused stitches spaced along the length of the end seal typically about ⅛ inch (center to center). Stitches 13a may be similarly dimensioned and spaced.

The three strips are intermittently fed forward between the horn 57 and the anvil 59 by the draw rolls 51 a predetermined distance corresponding to the desired tab length, with a dwell between successive feed cycles. During each dwell, the horn 57 is moved down from a raised retracted position (wherein it permits the forward feed of the strips) to a lowered position clamping the strips between the horn and the anvil, and more particularly clamping the strips down against the teeth at 65 and 67. The transducer 55 is energized ultrasonically to power the horn 57, and this effects sealing of each strip on the straight line of teeth 65 and the arcuate line of teeth 67 to form the arcuate end seal 17 at the trailing end of the leading tab 5 being formed from that strip, and the straight end seal 15 at the leading end of the next tab.

Figure 8:
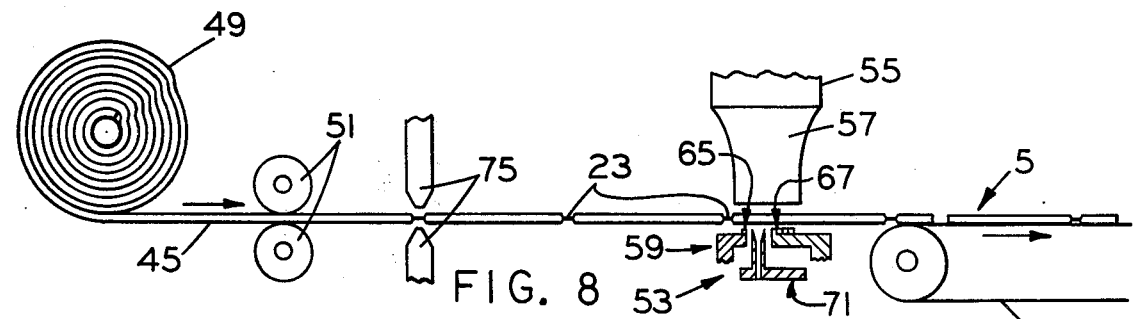
FIG. 8 is a diagrammatic side elevation illustrating further procedure in the manufacture of tabs of this invention.

The material of each of the three strips between the end seals 15 and 17 is cut out to segment the tabs 5 at the leading ends of the strips by a cutter generally designated 71 movable relative to the anvil in the opening 69 in the anvil between the teeth 65 and the teeth 67. At 73 in FIG. 8 is indicated a conveyor for carrying away the tabs severed from the strips.

Also in accordance with this invention, composite strips 45 are provided with the transverse scores 23 as they travel to the ultrasonic sealing and cutting apparatus 53. As shown in FIG. 8, these scores are formed by feeding the strips between upper and lower scoring knives each designated 75. During dwell intervals of strips 45, the knives 75 move together transversely to score the strips at the appropriate location relative to the tab ends later to be formed by apparatus 53.

Referring to FIGS. 12–15 showing detail of the ultrasonic sealing and cutting apparatus 53, the anvil 59 is shown to comprise a base plate 77 mounted in elevated position above a bed plate 79 on a pair of posts 81 extending up from the bed plate. The base plate has a rectangular opening designated 69a to form the aforesaid opening 69 in the anvil. Secured on the base plate 77 at one of the long sides of the rectangular opening 69a is a plate 83 having a groove 85 in the top along the side thereof toward the opening 69a. Each arcuate set of teeth 67 is formed on a jaw 87 secured in the groove 85 of plate 83 and extending from the plate 83 over the opening 69a. There are three of these jaws, located side-by-side. Each has an arcuate (e.g., semicircular) free end 89 and the teeth 67 are formed as integral parts of the jaw extending up from the jaw on the arc at its free end. Secured on the base plate 77 at the other long side of the rectangular opening 69 is an elongate jaw 91 having a flange 93 extending from the upper portion thereof over the opening 69a in the direction toward the jaws 87. This flange has a straight edge 95 spaced from the free ends 89 of the jaws, thereby forming upper portion 69b of the opening 69. Teeth 65 extend up from the flange at its edge. Jaw 91 is adjustable toward and away from jaws 87. It backs against adjustment screws 97 in a block 99 on plate 77, and is locked in adjusted position by screws 101.

The cutter 71 comprises a plate 103 having an elongate opening 105 therein corresponding generally to the shape of the opening 69b in the anvil. Thus, one long side of this opening is a straight line corresponding to the straight-line edge 95 of jaw 91, and the other long side is of scalloped form corresponding to the scalloped form of the free ends 89 of jaws 87. Extending up from the base plate 103 at the straight side of opening 105 is a cutter blade 107 having a relatively sharp upper edge, and extending up from the base plate 103 at the scalloped side of opening 105 is a cutter blade 109 of scalloped form corresponding to the scalloped form of the side of the opening 69 in the anvil defined by the free ends of jaws 87, these two cutter blades 107 and 109 having connecting webs 111 at their ends. Plate 103 is secured on a plate 113, the latter being slidably guided for up and down movement by posts 115 extending up from the bed plate 79. The cutter blade assembly is movable up and down in the opening 69 in the anvil, the straight blade 107 being movable contiguous to the edge 95 of jaw 91, and the scalloped blade 109 being movable contiguous to the arcuate free ends of the jaws 87.

Figure 13:
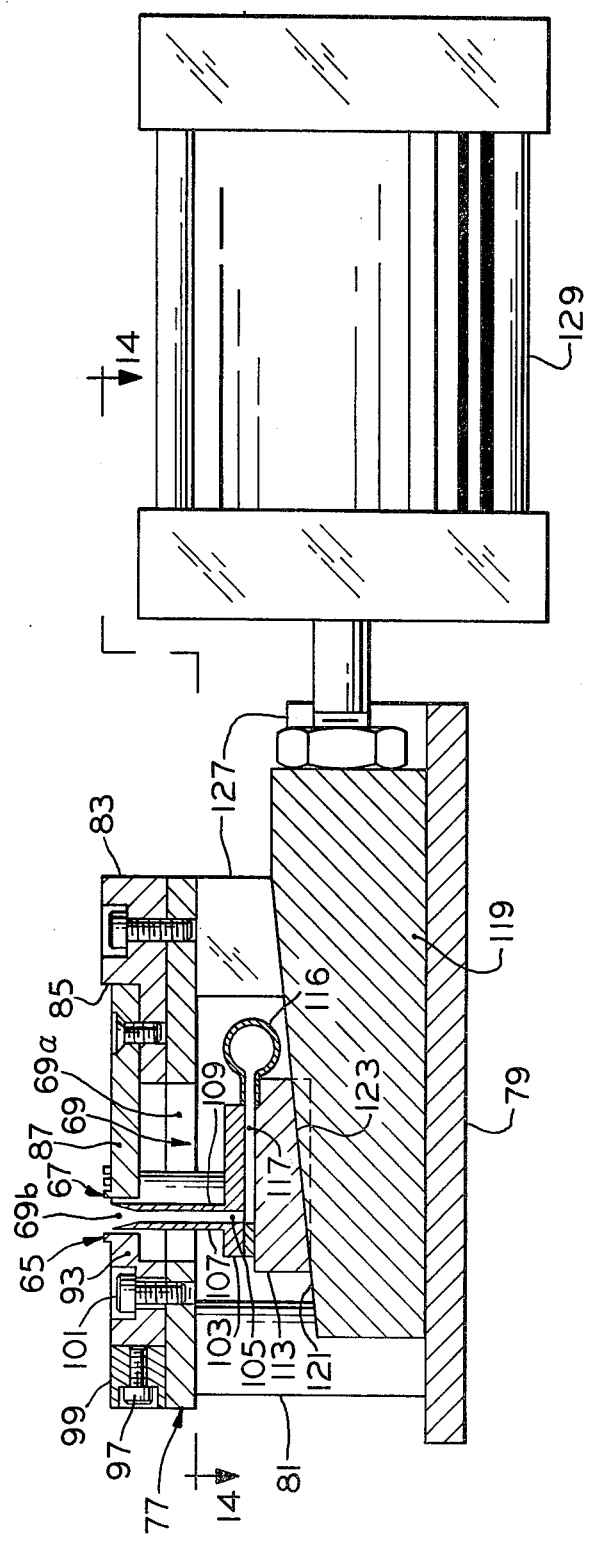
FIG. 13 is a vertical longitudinal section on line 13—13 of FIG. 12.

The cutter 71 is movable upwardly from the lowered retracted position in which it is shown in FIG. 13 to press the upper cutting edges of the blades 107 and 109 into the three composite strips 45 clamped between the horn 57 and the teeth 65 and 67 on the anvil to cut through the strips at the cutting edges of blades 107 and 109 while they are clamped and while they are ultrasonically activated by the horn, the blade 107 cutting the strips adjacent the straight ultrasonic seals 15 made by the teeth 65 and the blade 109 cutting the strips adjacent the arcuate ultrasonic seals 17 made by the teeth 67. As shown in FIG. 9, the strips 45 are fed over the anvil (and between the horn and the anvil, the horn being in a raised retracted position) in the direction such that the three arcuate end seals 17 are formed as the trailing end seals of a set of three tabs, and three straight end seals 15 are formed as the leading end seals of the next set of three tabs.

The cutting edges of the blades 107 and 109 are pressed into the composite strips 45 from the anvil side of the strips, completely cutting out the material between the seals 15 and the seals 17. The cut-out segment of material lodges in the cutter between the blades 107 and 109, and may be blown out by providing an air plenum 116 extending along one side of the cutter assembly and adapted to blow air into the space bounded by the blades 107 and 109 and the end webs 111 of the cutter via a passage provided by a groove 117 in the bottom of the plate 103. The plenum is supplied with compressed air from a suitable source (not shown) via a flexible air line 118 connected to one end of the plenum.

Means for moving the cutter 71 is shown to comprise a wedge 119 slidable on the bed plate 79 underneath the anvil 59 longitudinally in respect to the direction of feed of the strips 45 over the anvil. The wedge has a horizontal bottom face slidable on the plate 79, and a sloping upper face 121, and the plate 113 of the cutter assembly has a sloping bottom face 123 engaging the upper face 121 of the wedge, and side portions 125 extending down on opposite sides of the wedge forming a groove in the bottom of plate 113 receiving the wedge. The wedge is guided for sliding movement on the bed plate 79 by side guides 127 on the bed plate, and is operable by an air cylinder 129. FIG. 13 shows the wedge in a retracted position, and the cutter 71 down in its lowered retracted position. Cylinder 129 is operable to move the wedge toward the left from its FIG. 13 position to raise the cutter 71 for cutting the strips 45, and then to move back to its FIG. 13 position for lowering the cutter (which comes down under its own weight).

Figure 16:
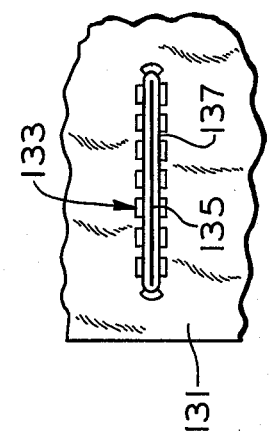
FIG. 16 is a view showing an adaptation of the apparatus for making buttonholes.
Figure 15:
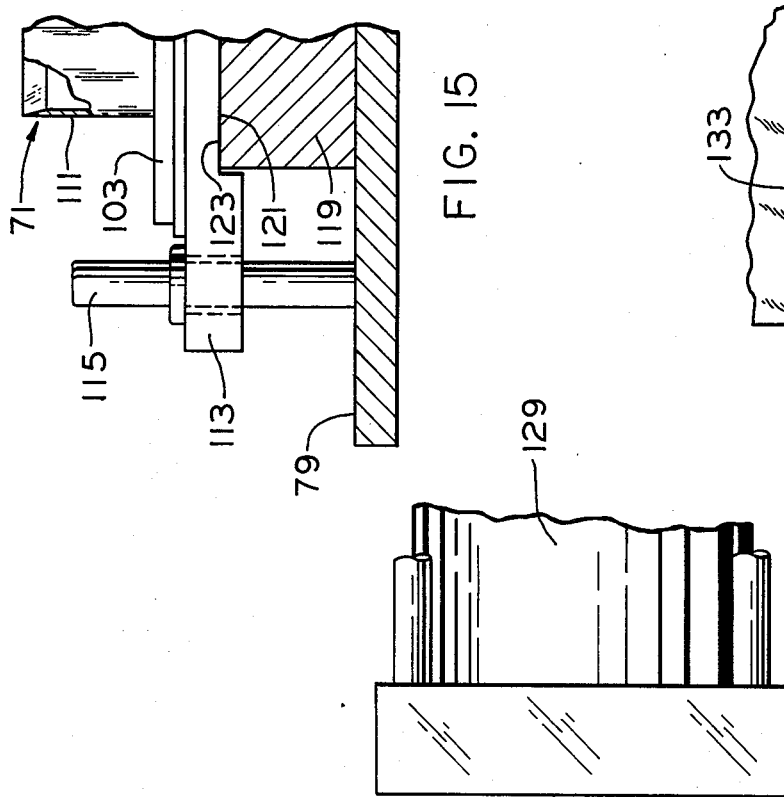
FIG. 15 is a vertical section on line 15—15 of FIG. 14.
Figure 14:
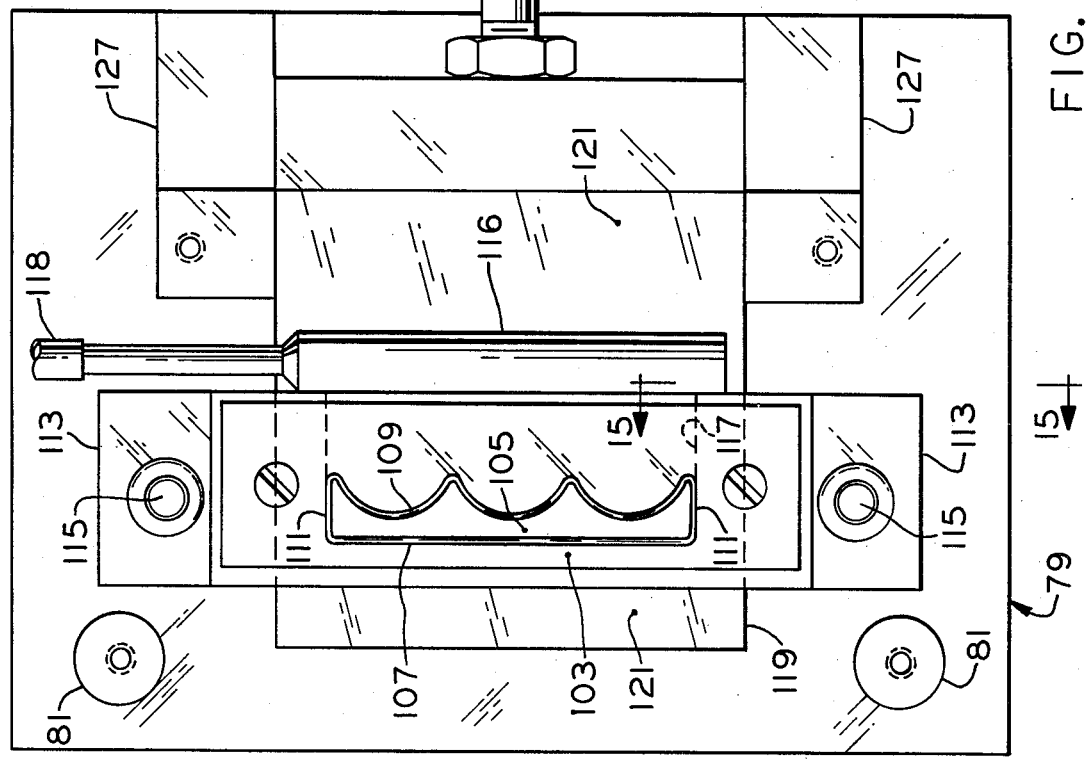
FIG. 14 is a horizontal section on line 14—14 of FIG. 13.

FIG. 16 shows an adaptation of the invention for making buttonholes, involving an anvil 131 having a pattern of teeth 133 for ultrasonically stitching a workpiece such as an item of apparel in a pattern for forming a buttonhole, and a cutter 135 operable in an opening 137 bounded by the pattern for cutting the item of apparel to form the actual hole of the buttonhole. The workpiece is clamped between the anvil and a horn like the horn 57, the horn is ultrasonically powered to form a buttonhole pattern of ultrasonically fused stitches corresponding to the pattern of the teeth 133, and the cutting edge of the cutter 135 is pressed into the workpiece within the buttonhole pattern of the stitches from the anvil side of the workpiece while the horn is powered to cut the workpiece to form the hole of the buttonhole within said pattern of stitches.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. A tab for a sanitary napkin belt comprising three layers of which the outer layers are of flexible ultrasonically sealable fabric and the intermediate layer is of flexible ultrasonically sealable padding material to constitute padding for the tab, the three layers being sealed together along each of their side edges and at each end thereof by a series of discrete thermoplastic stitches, and at least one score transverse to the length of the tab, the score being spaced from but adjacent to one end of the tab.

2. A tab as set forth in claim 1 wherein the outer layers are of polyester fabric.

3. A tab as set forth in claim 2 wherein the intermediate layer is also of polyester fabric but of heavier loft than the outer layers.

4. A tab as set forth in claim 3 wherein the intermediate layer is of a nonwoven polyester fabric.

5. A tab as set forth in claim 4 wherein the outer layers are also of a nonwoven polyester fabric.

6. A tab as set forth in claim 5 wherein the outer surfaces of the outer layers are relatively harder than the intermediate layer for abrasion resistance.

7. A sanitary napkin belt comprising an elastic waistband of ultrasonically sealable material and tabs as set forth in claim 6 secured to said waistband by discrete thermoplastic stitches.

8. The method of ultrasonically sealing and cutting tabs for sanitary napkin belts comprising clamping a workpiece between an anvil and an ultrasonic horn, the anvil having a raised pattern corresponding to the seal to be made and the ultrasonic horn being operable in conjunction with the anvil for forming ultrasonic seals, ultrasonically powering the horn for ultrasonically sealing the workpiece where it is clamped against said raised pattern by the horn, and, while the workpiece is clamped and the horn is ultrasonically powered, pressing a cutting edge into the workpiece from the anvil side toward the ultrasonic horn side of the workpiece to cut through the workpiece adjacent the ultrasonic seal made by the raised pattern while the workpiece is ultrasonically activated, the workpiece being in the form of a continuous strip, wherein said strip is a composite strip made by combining a plurality of strips and ultrasonically sealing the strips together along their side edges, the strip being intermittently, while the horn is in a retracted position, fed forward a predetermined distance with a dwell between successive feed cycles and clamped between the anvil and the horn during each dwell, the raised pattern on the anvil being such as to seal the strip on two lines spaced lengthwise of the strip, and the cutting edge being pressed into the strip between said lines of seal to sever the strip between said lines.

9. The method of claim 8 wherein the composite strip is made by combining three strips each of flexible polyester material one upon another with the intermediate strip being of heavier loft.

10. The method of ultrasonically sealing and cutting an ultrasonically sealable, continuous strip workpiece for making tabs for sanitary napkin belts comprising combining three strips each of flexible polyester material one upon another with the intermediate strip being of heavier loft, ultrasonically sealing the strips together along their side edges to form a composite, continuous strip workpiece, intermittently feeding the composite strip workpiece forward a predetermined distance with a dwell between successive feed cycles and clamping the workpiece between an anvil and an ultrasonic horn during each dwell, the anvil having a raised pattern corresponding to the seal to be made, the raised pattern on the anvil being such as to seal the strip on two lines spaced lengthwise of the strip, one of said two lines of seal being an arcuate line of seal extending from one side of the composite strip workpiece to the other and the other of said two lines of seal being a straight line of seal extending transversely of the composite strip workpiece from one side of the composite strip workpiece to the other spaced from but adjacent the arcuate line of seal on the convex side of the arcuate seal, ultrasonically powering the horn for ultrasonically sealing the composite strip workpiece where it is clamped against said raised pattern by the horn, and, while the workpiece is clamped and the horn is ultrasonically powered, pressing a cutting edge into the workpiece between said lines of seal from the anvil side of the workpiece to cut through the workpiece transversely from one side of the composite strip to the other between said lines of seal while it is ultrasonically activated adjacent the ultrasonic seal made by the raised pattern.

11. The method of claim 10 wherein the composite strip is scored on a line extending transversely of the composite strip adjacent the straight-line seal on the side of the straight-line seal opposite the arcuate seal.

12. The method of claim 10 wherein the strips are ultrasonically stitched together along their side edges, and along said arcuate and straight lines of seal by discrete ultrasonically fused stitches.

13. The method of making tabs for sanitary napkin belts comprising combining three strips of flexible ultrasonically sealable material with the outer strip being of ultrasonically sealable fabric and the intermediate strip being of ultrasonically sealable padding material to constitute padding for the tabs, ultrasonically stitching the three strips together along their side edges, intermittently feeding the resultant composite strip forward a distance corresponding to the desired tab length with a dwell between successive feed cycles, clamping the composite strip between an anvil and an ultrasonic horn during each dwell, the anvil being formed to stitch the three strips of the composite strip together on two lines spaced lengthwise of the composite strip forming a trailing end seal of one tab and a leading end seal of the next tab, powering the horn to form said seals, and pressing a cutting edge into the composite strip between said lines from the anvil side of the composite strip while the horn is powered to cut through the composite strip between said seals.

14. The method of claim 13 wherein one end seal is straight and the other is curved, and the cutting edge cuts out the material between said seals.

15. The method of claim 14 wherein the cut-out material is blown away.

16. Apparatus for ultrasonically sealing and cutting an ultrasonically sealable workpiece in the form of a continuous strip comprising an anvil having a raised pattern corresponding to the seal to be made and an ultrasonic horn relatively movable toward and away from one another, the raised pattern on the anvil comprising two lines of projections on the anvil, said lines being spaced lengthwise relative to the strip, said anvil having an opening between said lines, one of said lines of projections being an arcuate line for sealing the strip from one side thereof to the other and the other of said lines of projections being a straight line of projections for sealing the strip from one side thereof to the other spaced from but adjacent the arcuate line of projections on the convex side of the arcuate line of projections, the horn being adapted to clamp a workpiece against the raised pattern on the anvil when the horn and anvil are moved relatively to one another, means for ultrasonically powering the horn for ultrasonically sealing the workpiece where it is clamped against said raised pattern by the horn, means for intermittently feeding the strip forward a predetermined distance with a dwell between successive feed cycles, the strip being clamped between the anvil and the horn during each dwell, and a cutter associated with the anvil and operable in the opening thereof having an arcuate cutting edge adjacent the arcuate line of projections and a straight cutting edge adjacent the straight line of projections, said cutter being movable relative to the anvil to press its cutting edge into the workpiece from the anvil side of the workpiece to cut through the workpiece while it is ultrasonically activated adjacent the ultrasonic seal made by the raised pattern.

17. Apparatus as set forth in claim 16 wherein the cutter has a straight blade having said straight cutting edge, and a curved blade having said arcuate cutting edge spaced from the straight blade, and means for blowing material cut from the workpiece out from between said blades.

* * * * *